United States Patent
Kunze et al.

(10) Patent No.: US 8,259,896 B2
(45) Date of Patent: Sep. 4, 2012

(54) EFFICIENT CORRECTION OF POLYCHROMY EFFECTS IN IMAGE RECONSTRUCTION

(75) Inventors: Holger Kunze, Bubenreuth (DE); Holger Scherl, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/889,718

(22) Filed: Sep. 24, 2010

(65) Prior Publication Data

US 2011/0075899 A1    Mar. 31, 2011

(30) Foreign Application Priority Data

Sep. 28, 2009  (DE) .......................... 10 2009 043 213

(51) Int. Cl.
*A61B 6/00*        (2006.01)
(52) U.S. Cl. ............................................... 378/4; 378/5
(58) Field of Classification Search .............. 378/5, 98.9; 382/128, 130
See application file for complete search history.

(56) References Cited

U.S. PATENT DOCUMENTS

| | | | | |
|---|---|---|---|---|
| 4,217,641 | A * | 8/1980 | Naparstek ..................... | 382/131 |
| 4,626,991 | A * | 12/1986 | Crawford et al. ................. | 378/4 |
| 4,709,333 | A * | 11/1987 | Crawford ..................... | 600/425 |
| 5,243,664 | A * | 9/1993 | Tuy .............................. | 382/130 |
| 603,501 | A | 3/2000 | Hsieh | |
| 6,771,733 | B2 | 8/2004 | Katsevich | |
| 6,845,142 | B2 | 1/2005 | Ohishi | |
| 2003/0161521 | A1* | 8/2003 | Newport et al. ............ | 382/131 |
| 2004/0101090 | A1* | 5/2004 | Drummond et al. ............. | 378/4 |
| 2006/0067460 | A1* | 3/2006 | Price et al. ....................... | 378/5 |
| 2006/0285630 | A1 | 12/2006 | Bernhardt et al. | |
| 2007/0090300 | A1* | 4/2007 | Sibomana et al. ........ | 250/370.09 |
| 2008/0095300 | A1* | 4/2008 | Zingelewicz et al. ............. | 378/4 |
| 2008/0273651 | A1 | 11/2008 | Boas | |

OTHER PUBLICATIONS

Buzug: Einführung in the Computertomographie: 1. Auflage 2004 [Introduction to Computed Tomography: 1st edition]. Springer. ISBN 3-540-20808-9.
Van De Casteele: "Model-based approached for Beam Hardening Correction and Resolution Measurements in Microtomography", Dissertation, University of Antwerp, 2004.
Bal and Spies: "Metal artefact reduction in CT using tissue-class modeling and adaptive prefiltering", Med. Phys. 33(8), 2006.
Siddon: "Fast calculation of the exact radiological path for a three-dimensional CT array", Medical Physics, 12(2):252-255, Mar. 1985.
Mueller: "Fast and accurate three-dimensional reconstruction from Cone-Beam projection data using Algebraic Methods", Dissertation, Ohio State Univ., 1998.
Van De Casteele et al., "An energy-based beam hardening model in tomography", Physics in Medicine and Biology, 2002, pp. 4181-4190, vol. 47.

* cited by examiner

*Primary Examiner* — Alexander H Taningco

(57) ABSTRACT

A method for determining absorption coefficients corrected with polychromy artifacts for an object composed of a plurality of material types differentiated with absorption attributes is provided. A plurality of x-ray beam projections of the object are recorded with monochrome x-rays from different positions. The recorded projections are reconstructed to determine a first set of absorption coefficients. The projections are calculated by reprojection. The recorded projections are corrected by the calculated projections. A second set of absorption coefficients corrected with polychromy artifacts is finally determined by reconstructing the corrected projections. A formula-based description of a rule taking account of polychromy is used in the calculation. The rule includes parameters to be determined by the reprojection in the course of the calculation of projections. The method combines steps of conventional methods and is thus more efficient.

4 Claims, 6 Drawing Sheets

EFFICIENT CORRECTION OF POLYCHROMY EFFECTS IN IMAGE RECONSTRUCTION

CROSS REFERENCE TO RELATED APPLICATIONS

This application claims priority of German application No. 10 2009 043 213.2 filed Sept. 28, 2009, which is incorporated by reference herein in its entirety.

FIELD OF THE INVENTION

The invention relates to a method, a device and a computer program for determining absorption coefficients corrected in respect of polychromy artifacts for an object composed of a plurality of material types which differ in respect of the absorption attributes.

BACKGROUND OF THE INVENTION

Computed tomography (CT) makes available a diagnostic and measurement procedure for medicine and test engineering, with the aid of which internal structures of a patient and test object can be examined, without thereby having to perform operational interventions on the patient or having to damage the test object. In this case a number of projections of the object to be examined are recorded from different angles. A 3D description of the object can be calculated from these projections.

FIG. 1 shows a typical CT arrangement with an x-ray source 1 in a first position, which transmits an x-ray beam 2 for a first projection, said beam being detected in a detector 3 at a first position, after it has penetrated the object to be examined 4. The data of the detector arrives at an evaluation computer 5 which undertakes the reconstruction, and is then displayed on a display unit 6. The x-ray source ideally moves on a circular path, with numerous projections being recorded. FIG. 1 shows by way of example the x-ray source in a different position 11, with an x-ray beam 12 being transmitted for a different projection and then being detected in the detector at a different position 13.

During the subsequent processing of the measured data it is assumed that the Lambert-Beer law $$I = I_0 \exp\left(-\int_{beam} \mu(s) ds\right)$$

applies for the measured data. Here I represents the intensity measured by means of the detector 3, $I_0$ the unattenuated intensity and $\mu(s)$ the attenuation coefficient at the location s. However, this relationship applies only for monochromatic radiation and not for the polychromatic radiation of an x-ray tube. Instead the relationship dependent on the photon energy E applies for this $$I = \int_{E=0}^{E_{max}} dE I_0(E) \exp\left(-\int_{Beam} \mu(s, E) ds\right)$$

If this dependency is not taken into account, the reconstructed image has artifacts which distort the reconstructed attenuation value by up to several percentage points (compared to a reconstruction from measured data obtained monochromatically) [Buz04].

Various methods are known in the literature for how values approximately independent of the photon energy can be calculated from the values measured in this way. The method relevant to this application is of an iterative nature and is outlined in the following.

It is first assumed that the data was recorded monochromatically. A reconstruction of the object is calculated. Then the object is segmented into different regions (for example soft tissue and bone). Several approaches are described for this in the literature. In the simplest case this can be done by means of a threshold procedure.

Artificial projections are now calculated for each tissue class from the images segmented in this way. Relevant items of information in each case are the attenuation proportion and the beam length of each x-ray beam through the segmented tissue portion.

A correction factor can be ascertained from the determined projection values and/or material thicknesses of the individual tissue classes, with which the originally measured value can be corrected, before a second, final reconstruction of the object is calculated [Cas04]. The correction procedure is illustrated diagrammatically in FIG. 2 for three different tissue classes.

Metal-like elements such as tooth implants or artificial hips create such strong artifacts that it may be that the procedure described can no longer be used. A metal artifact correction procedure is described in [Bal06] which likewise requires the calculation of different projection images through various tissue classes. In a first step those regions whose associated beams run through metal are determined on the projection image. In a second step a projection image of a model volume is determined. In the model volume metal regions are replaced by adjacent tissue classes. On the basis of both these projections the original projection values can now be corrected, so that an artifact-free image can be reconstructed. This procedure is summarized diagrammatically in FIG. 3.

The projection calculation can be performed as follows: the image is divided into rectangular pixels which in each case have the value of the attenuation coefficient at the associated scanning point across the entire pixel surface. The line integral along the beams can then be weighted as a sum of the scan values with the irradiated length through the associated pixels [Sid85]. This procedure is illustrated in FIG. 4.

Other projection algorithms are know from the literature which differ from the described method by the calculation of the weight with which a pixel is used in the projection calculation [Mue98].

In the procedures described at least two projection calculations are necessary. Furthermore, in addition to the memory for the object a further memory for the segmented objects must be kept available.

SUMMARY OF THE INVENTION

The object of the invention is to improve the efficiency of conventional methods for correction of polychromy artifacts.

The object is achieved by the claims.

According to the invention a method is proposed for determining absorption coefficients corrected in respect of polychromy artifacts for an object composed of a plurality of material types differing in respect of the absorption attributes. In the case of the method a plurality of x-ray beam projections is recorded for the object from different positions. By reconstructing the recorded projections a first set of absorption coefficients is determined, the reconstruction using an absorption rule applicable for monochrome x-ray radiation. A reconstruction method, e.g. filtered backprojection, Feldkamp algorithm, algebraic reconstruction techniques (ART/SART), Grangeat method or Fourier method, is used for the reconstruction.

Projections are then calculated by means of reprojection. The recorded or measured projections are corrected using the calculated projections in the sense of projections recorded with monochrome x-ray beams. Finally a second set of absorption coefficients corrected in respect of polychromy artifacts is determined by reconstruction on the basis of the corrected projections. For the correction use is made of a formula-based description of a rule taking account of polychromy which comprises parameters to be determined. According to the invention the parameters are determined in the course of or during the calculation of projections by means of reprojection or in parallel, contemporaneously or simultaneously thereto.

The invention permits a more efficient correction of polychromy artifacts. In contrast to conventional methods, which first determine the formulae for the attenuation of the polychrome radiation and then perform the projection calculation (reprojection), in accordance with the invention the formulae are constructed as part of the projection calculation. In particular, no additional projections need be performed in order to determine formula parameters.

According to a preferred embodiment of the invention a segmentation of a volume of the object is undertaken in the course of the calculation of projections by means of reprojection.

This embodiment permits an even less complex implementation, since only one projection step needs to occur for the calculation of the projection values and furthermore no additional memory need be created for the segmentation. The extra effort required for the segmentation during the projection calculation remains negligible thanks to the use of a pipeline structure. Both the calculation time and the resource requirement are significantly reduced thanks to the proposed solution.

According to a development a correction to prevent metal artifacts is performed in the course of the calculation of projections by means of reprojection.

The invention also includes a device for implementing an inventive method. The proposed modified methods are particularly suitable for an implementation on special hardware based on FPGA and/or ASIC technology. Other special hardware (such as DSP solutions or special processors such as the cell broadband engine or graphic accelerator) can likewise be employed in the proposed approach.

BRIEF DESCRIPTION OF THE DRAWINGS

The invention is described in greater detail in the following in the context of exemplary embodiments on the basis of figures. These show.

DETAILED DESCRIPTION OF THE INVENTION

Figure 1:
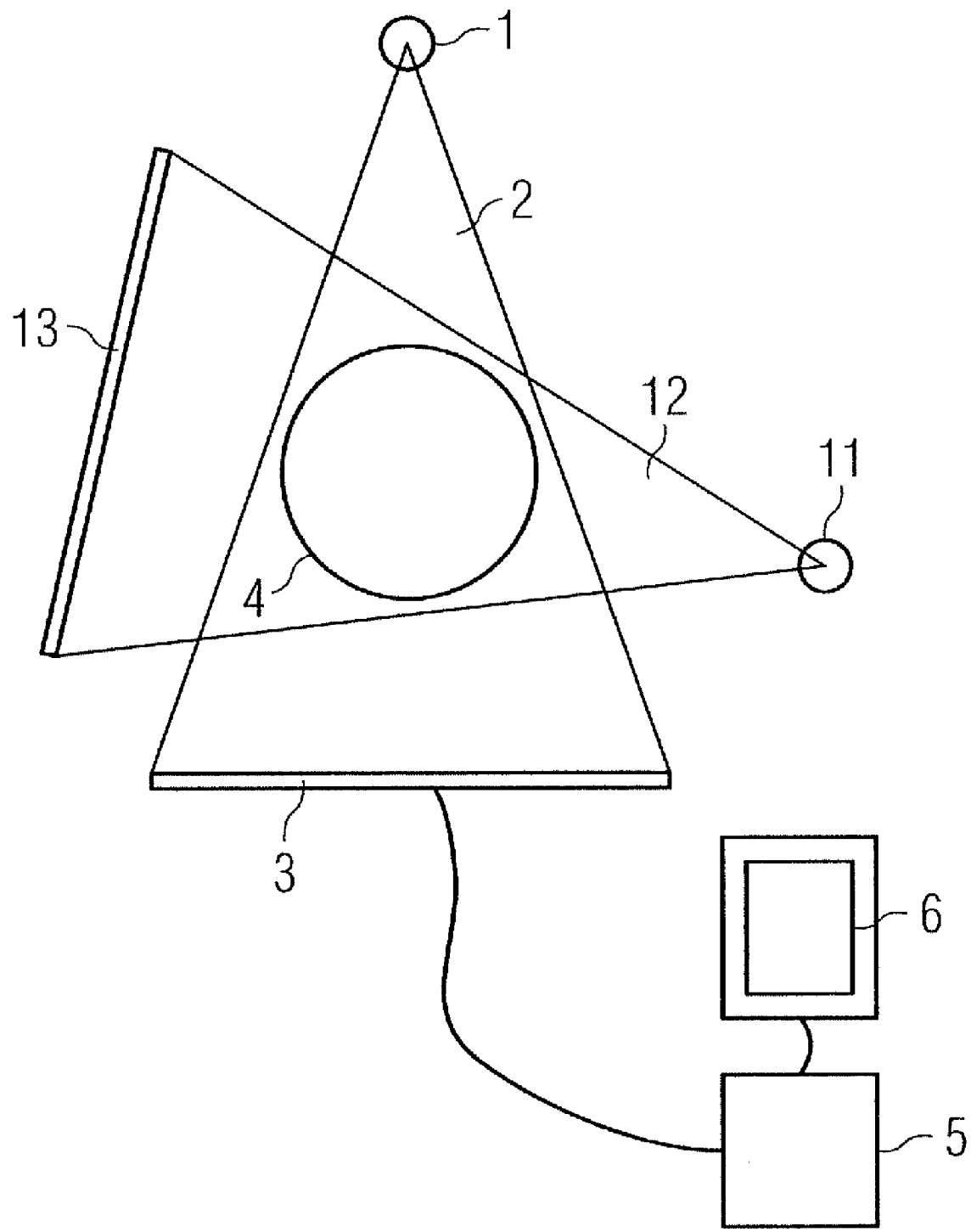
FIG. 1: Typical arrangement for CT recordings
Figure 2:
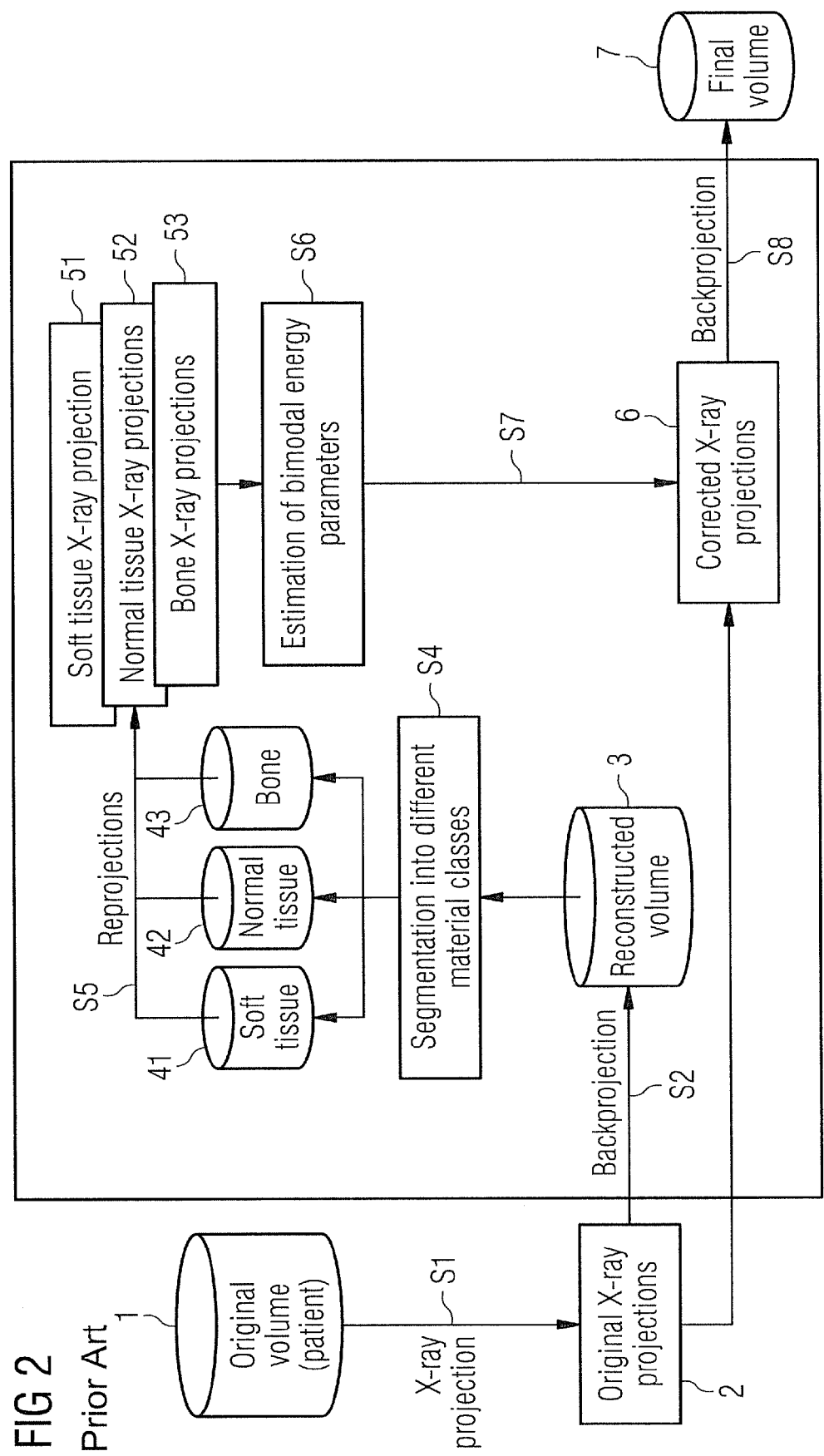
FIG. 2: Correction method for polychromy artifacts

FIG. 2 shows a conventional method for determining absorption coefficients, corrected in respect of polychromy artifacts, for objects which are composed of a plurality of different material types. In the following more detailed description of this method the presentation is geared to the bi-modal energy model specified in Cas04. The sequence of such a method is also illustrated in particular in FIG. 5.2 of the cited source. As a point of departure for the method a plurality of x-ray beam projections 3 is recorded from different positions or directions (step S1). The projections or sinograms 2 obtained in this way form the basis for the reconstruction of the object 1, or more precisely of the absorption attributes of the examined object 1. The projections are first used for a backprojection S2. This is based on monochrome x-ray radiation, i.e. it presupposes the validity of the Lambert-Beer law. As a result of this backprojection (for an example of a method for backprojection see U.S. Pat. No. 6,771,733 B2) a first set of attenuation coefficients 3 is obtained for the object 1, which are corrected in respect of the polychromy of the beam used.

This set of attenuation coefficients or this object reconstruction 3 is segmented into various material classes or material types in a next step S4. This segmentation corresponds to a classification, i.e. each of the reconstructed absorption coefficient values is assigned a material class. The individual material classes differ—as stated above—by their absorption attributes, i.e. materials which differ only in physical attributes other than the absorption capacity are treated here as one material class. FIG. 2 shows by way of example three different material classes, namely soft tissue 41, normal tissue 42 and bone 43. This classification can for example be performed using what is known as a threshold value procedure. This is based on the significant changes in the absorption rate for various material types. Afterwards, as described in [Cas04], the thickness of the object 1 is determined for a direction, differentiated by sections with various tissue types. After segmentation and determination of the thickness a reprojection S5 is performed (for the corresponding direction). This consists of simulated irradiation with x-rays. A calculation for a plurality of parallel beams normally takes place here, with the position of the beams in the plane being oriented perpendicularly to the direction of the radiation and their thickness to the detector conditions. This reprojection S5, with the aid of a mathematical approach for the attenuation of polychromatic x-ray radiation, simulates the beam attenuation or projections during irradiation of the individual tissue types 51, 52, 53. The mathematical approach depends on parameters, the determination of which is the aim of this simulation. A bi-modal energy model described in [Cas04] can for example be used as a model for the corresponding attenuation or absorption of polychrome x-ray radiation, in which for physical reasons two dominant energies in the beam can be assumed.

A mathematical expression for the attenuation of the intensity in accordance with this model is shown for example in equation 3.6 in [Cas04]. However, a non-physically motivated approach is also possible for example, which uses suitable approach functions for the description of the corresponding attenuation curves. As described in [Cas04], the intensity attenuation is now determined along the individual beams section by section for the various material types. It must be taken into account here that material regions located in the interior of the object can be screened by regions of a different type of material located further outward. This screening must be taken into account when calculating the beam intensity attenuation. This occurs, e.g., in that for the attenuation contribution of a region located further inward it is taken into account that the intensity of the beam is already attenuated when it reaches this region, it being possible for this attenuated intensity to be expressed mathematically by the approach used. Thus for the intensity of a beam following penetration of the whole object an expression is obtained which depends on the mathematical approach used and its parameters for the individual material layers and their thickness. Unknown variables here are the parameters for the individual material layers. This expression for the intensity attenuation is then equal to the intensity attenuation measured by the detector for a plurality of beams, a plurality equation system with the parameters of the tissue classes as unknowns. This equation system is generally overdetermined and can be resolved as a minimization problem by minimizing the differences and calculated intensity attenuation. In this way the values for the parameters are determined (step S6), with which a formula-based correlation for the intensity attenuation of the polychrome x-ray radiation is present.

By means of this mathematical description for the attenuation of polychrome radiation the measured projection data is corrected as regards the polychromy of the x-ray radiation, i.e. corrected such that it corresponds to data recorded during polychrome x-ray radiation (step S7). Corrected projections 6 are obtained. A backprojection (step S8) is then performed, for which Beer's law is now correctly applied. This produces a second set of attenuation coefficients 7, now corrected in respect of monochromy, i.e. the final reconstruction of the object.

Figure 3:
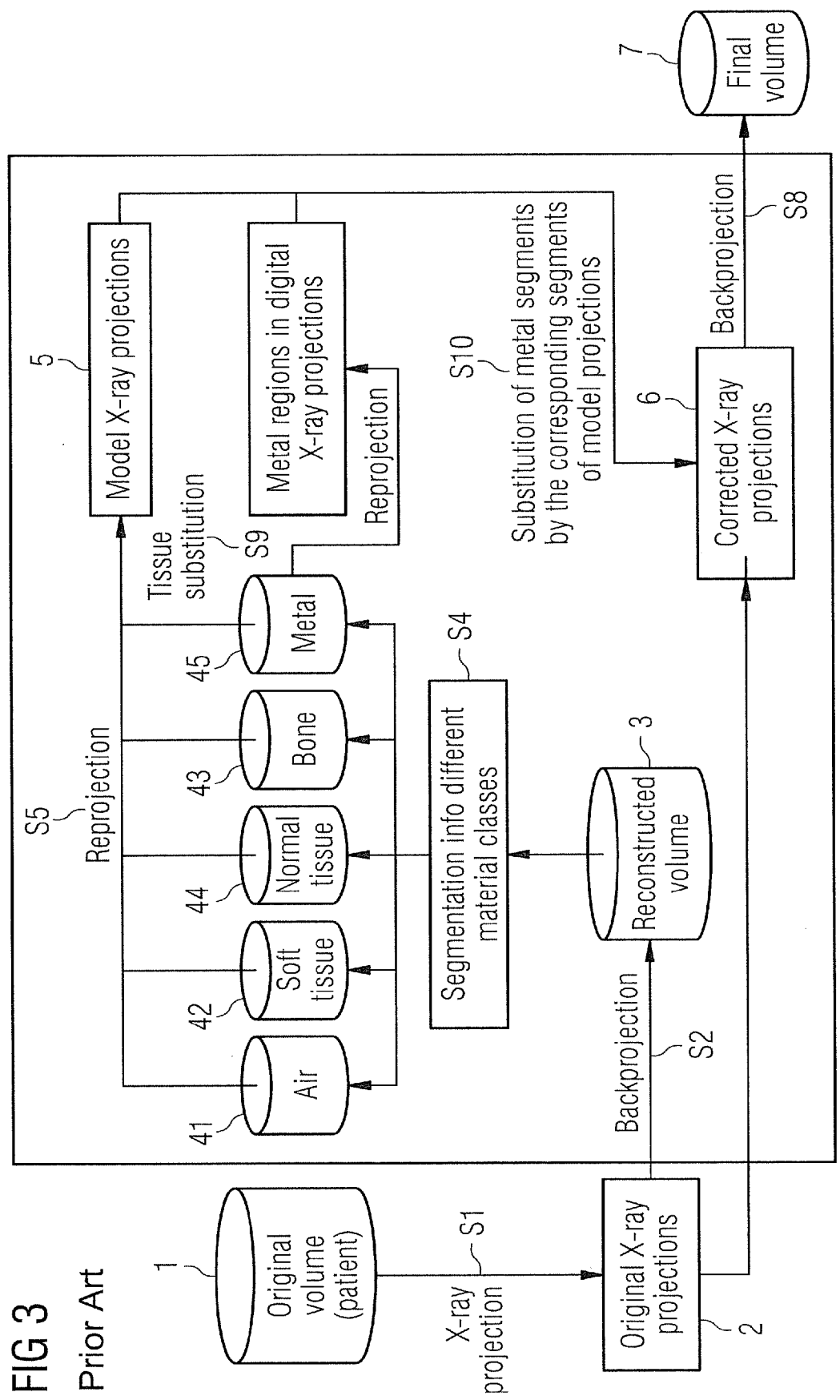
FIG. 3: Correction method for polychromy artifacts with additional correction of metal artifacts

FIG. 3 shows an amplification of conventional methods for correction, in which metal regions of the object are dealt with (additionally in classification: normal tissue 44 and metal 45; the projections for calculating the rules for polychromatic radiation for the various tissue types apart from metal are designated by reference character 5). Such a method is described in more detail in [Bal06]. The motivation for this development is primarily that during tissue examinations metal is irradiated from time to time, for example in the form of metal prostheses, surgical clamps or tooth fillings. These result in considerable interference. Shown in simplified form, the development comprises removing regions identified as metallic during segmentation for the simulation of the attenuation and modeling material types located in the vicinity (step S9 in FIG. 3). It is apparent that the calculated attenuation value for a beam, in which metallic material was replaced by surrounding material in the simulation, can no longer correspond to the measured one, since the replaced material has a different absorption attribute. The calculated attenuation value for such beams is hence not used for the optimization problem, which does not represent a problem inasmuch as the optimization problem exists in an overdetermined equation system. In contrast, in the course of the correction for beams penetrating metallic regions the measured value is replaced by the calculated one, in which the influence of the metal has been removed (step S10 in FIG. 3). Thus a set of projection data (supplemented by the substitution of the calculated beams) is obtained which consists partly of measured and partly of simulated data (namely for the metallic regions). Again a correction of the projection data is performed with regard to the polychromy and the corrected data set is obtained afterwards in a backprojection.

The invention is based on the observation that with such a method efficiency can be increased, in that steps are performed in parallel. Conventionally the following steps are performed sequentially:
   a. segmentation of the volume (step S4 from FIG. 2)
   b. calculation of intensity attenuation of the polychrome beams by the tissue classes used and determination of rules for the attenuation of the polychromatic radiation (steps S5 and S6 from FIG. 2)
   c. calculation of the correction (step S7 from FIG. 2)

According to the invention steps b. and c. are performed in parallel. In a development described in detail below all three steps a.-c. are performed (at least partially) in parallel.

Figure 4:
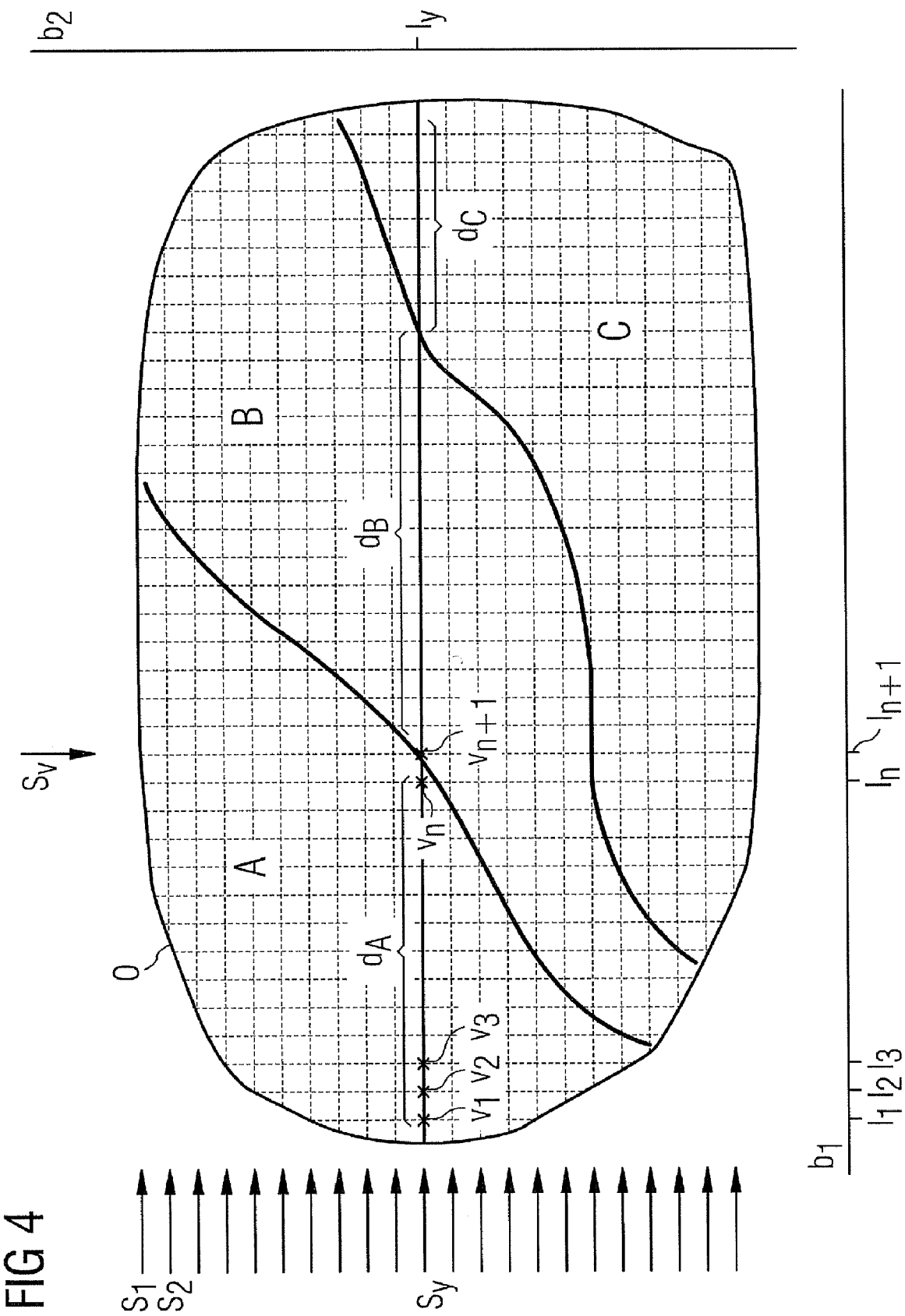
FIG. 4: Illustration of an inventive method

Principles of a possible procedure are explained on the basis of FIG. 4. This involves an outline presentation which for the sake of comprehensibility does not reproduce more complex details of real applications.

An object O is shown which is examined using x-ray radiation. The object O is represented as a grid, with points of intersection of the grid lines representing voxels or pixels, i.e. positions for which the attenuation coefficient $\mu$ is determined. The voxels $v_1$, $v_2$, $v_3$, $v_n$ and $v_{n+1}$ are named by way of example.

At bottom right in the drawing two detector positions $D_1$ and $D_2$ are shown, for which recordings (irradiation of the object O with x-ray radiation) are performed. In reality considerably more recordings are performed. Furthermore the distance between the detector positions $D_1$ and $D_2$ does not correspond to the real circumstances.

The detector (radiation detector) normally consists of individual elements (photocell, photomultiplier, CCD sensor, etc.) which register radiation intensities. The size and arrangement of the elements determine the granularity of the recording, i.e. each element and thus the position of each element is assigned a measured intensity value. By way of example the positions where intensity measurements are undertaken are indicated for the detector position $D_1$ by means of vertical dashes. By way of example the measured intensities $I_1, I_2, I_3, I_n, I_{n+1}$ and for the detector position $D_2$ the intensity $I_y$ are drawn in. These measurement results form the basis for the reconstruction of the object O, i.e. for determining the attenuation coefficient $\mu$ (also designated as grayscale values with respect to a visualization of the object O). The object O is composed of three different material types A, B and C.

The object of the invention is to reconstruct the attenuation coefficient $\mu$, taking into account the polychromy of the radiation used during the measurement. The procedure is as follows:

The object is first reconstructed without taking account of polychromy effects. This is done by using "filtered backprojection", which assumes the validity of the Lambert-Beer law. Methods for this are described e.g. in Bu04. This produces a first set of (not corrected) attenuation coefficients $\mu_1(v_i)$ for all voxels $v_i$. This first set of attenuation coefficients is used for the segmentation.

The segmentation corresponds to a classification in respect of the material class, i.e. in the present case an assignment to one of the material types A, B or C. For the segmentation e.g. a threshold value method or a clustering method is used. This divides the scale for possible attenuation values into regions. Those attenuation values which lie in the same region are then also assigned to the same material class.

The segmentation can take place as a separate step after the backprojection. However, in the context of this exemplary embodiment it is performed in the course of the reprojection.

A reprojection occurs after the reconstruction of the first set of attenuation coefficients. This reprojection simulates the real beam intensity attenuation. In other words, the Lamber-Beer law is no longer used to determine the attenuation. Instead a mathematical approach is made, by means of which the polychromy of the radiation is taken into account. This approach can, but need not, be made in line with physical principles. Examples of such a description can be found in Cas04. A corresponding formula for the intensity attenuation looks as follows:

$I(d)=f(I_o,d,\alpha_{M,i})$, where $I_o$, represents the initial intensity of the beam, $d$ the thickness of the penetrated material and $\alpha_{M,i}$ parameters.

The index i here differentiates between the parameters used, e.g. i from $\{1,2,3\}$. It is assumed here for simplicity that all parameters depend on the material type M (i.e. M is from the set $\{A,B,C\}$ in the present case). The parameters $\alpha_{M,i}$ are of course also dependent on the beam attributes (energy spectrum) of the beam used for the measurement. However, this need not be taken into account as an explicit dependency in the following.

The reprojection results from a simulated irradiation of the object O. This simulated irradiation emulates the measurement made at the outset. Position and number of the beams are correspondingly geared to the measurement results, i.e. for each registered measured value the attenuation of a beam is simulated. This plurality of beams is indicated by arrows on the left of the figure. By way of example, reference characters are specified for the beams $S_1$, $S_2$ and $S_y$. For simplicity's sake only one beam. $S_v$ is indicated for the vertical direction, although a plurality of beams is also simulated in this direction.

The procedure is now followed step by step or voxel by voxel. The voxel $v_1$ is assigned to material class A using threshold value methods. As from the second step or the second voxel $v_2$ an additional check is made to see whether a change of material class has occurred. A change of material class is detected in the case of a transition from voxel $v_n$ to voxel $v_{n+1}$. This triggers the material thickness calculation. The thickness of the penetrated layer of material type A is calculated from the product of the number of steps and the step width. In this way the voxels are classified and the penetrated thicknesses $d_A$, $d_B$ and $d_C$ are calculated. When the end of the object is reached, a mathematical description of the intensity attenuation of the beam is made. Using the formula $I(d)=f(I_o,d,\alpha_{M,i})$ and the observation that internal layers are screened, i.e. experience a reduced intensity, gives for the calculated intensity $I_d$ after penetration of the object:

$$I_d=f(f(f(I_o,d_A,\alpha_{A,i})d_B,\alpha_{B,i}),d_C,\alpha_{C,i}) \quad (1)$$

Equalizing measured and calculated intensity ($I_d=I_y$) for a plurality of beams produces an overdetermined equation system, from which the parameters $\alpha_{M,i}$ are determined by minimizing the deviations between measured and calculated values.

The descriptions obtained in this way for the effect of polychromy are used to correct the measured data (e.g. measured intensities $I_1$, $I_2$, $I_3$, $I_{n+1}$, so that a renewed filtered backprojection based on the Lambert-Beer law produces corrected attenuation coefficients.

It is expedient, because of the number of parameters, to resolve the equation system step by step using a corresponding selection of equations.

First the thicknesses of the penetrated layers are determined for the individual beams S. This is described below on the basis of the beam $S_y$. The procedure moves step by step (in the figure the step width is selected according to the voxel spacing) along the beam $S_y$, a classification of the voxel being performed for each voxel ($v_1$, $v_2$, $v_3$, ... $v_n$, $v_{n+i}$ ...). Simultaneously a check is made to see whether the tissue class changes. At the transition from voxel $v_n$ to voxel $v_{n+1}$ a tissue transition is noted. The irradiated length of the tissue A is calculated and saved at this point. The procedure continues accordingly, until the object O is penetrated.

As a result of this simulation of the beam $S_y$ the following is obtained:

the irradiated tissue thicknesses $d_A$, $d_B$, $d_C$ classifications, i.e. a tissue assignment for the voxels located on the beam the simulated projection or calculated intensity after penetration of the object.

This is performed for all beams of all projections. The classification can in this case be terminated if all voxels are classified. In the present example the classification is already complete with the simulation of the beams for one of the two projections illustrated.

The (calculated) beam intensities are determined using the thicknesses $d_A$, $d_B$, $d_C$. The equation system (1) could be resolved here generally. A better procedure to follow consists in a step by step resolution which deals with the tissue types consecutively, with beams first being selected which irradiate only one tissue type (in the present case A).

In other words, beams S are sought, for which the following applies for the determined thicknesses $$d_A>0, d_B=0, d_C=0.$$

Formula (1) is then reduced to $$I_d=f(I_o,d_A,\alpha_{A,i}) \quad (2)$$

Equating measured and calculated intensity ($I_d=I_y$) produces $\alpha_{A,i}$ as the result of an optimization problem for a sufficient number of beams for which (2) applies. The next step is to search for beams S for which the following applies for the determined thicknesses $$d_A \geq 0, d_B>0, d_C=0.$$

Formula (1) is then reduced to $$I_d=f(f(I_o,d_A,\alpha_{A,i}),d_B,\alpha_{B,i}) \quad (3)$$

Since the $\alpha_{A,i}$ are already determined, equating measured and calculated intensity produces an equation system with merely the $\alpha_{B,i}$ as unknowns. In this way the intensity attenuation is calculated consecutively for the individual tissue types. Thus all intensities $I_d$ can be obtained and used for the correction of the measured values (step ... in FIG. 3).

The procedure can be amplified to the situation shown in FIG. 4, i.e. when metal artifacts are present, in that during the beam simulation voxels which were assigned to a metal are replaced by voxels of an adjacent tissue type.

In FIG. 4 the beams are selected so that the voxels lie on the beams. This is not necessary, as is made clear on the basis of FIG. 5.

Figure 5:
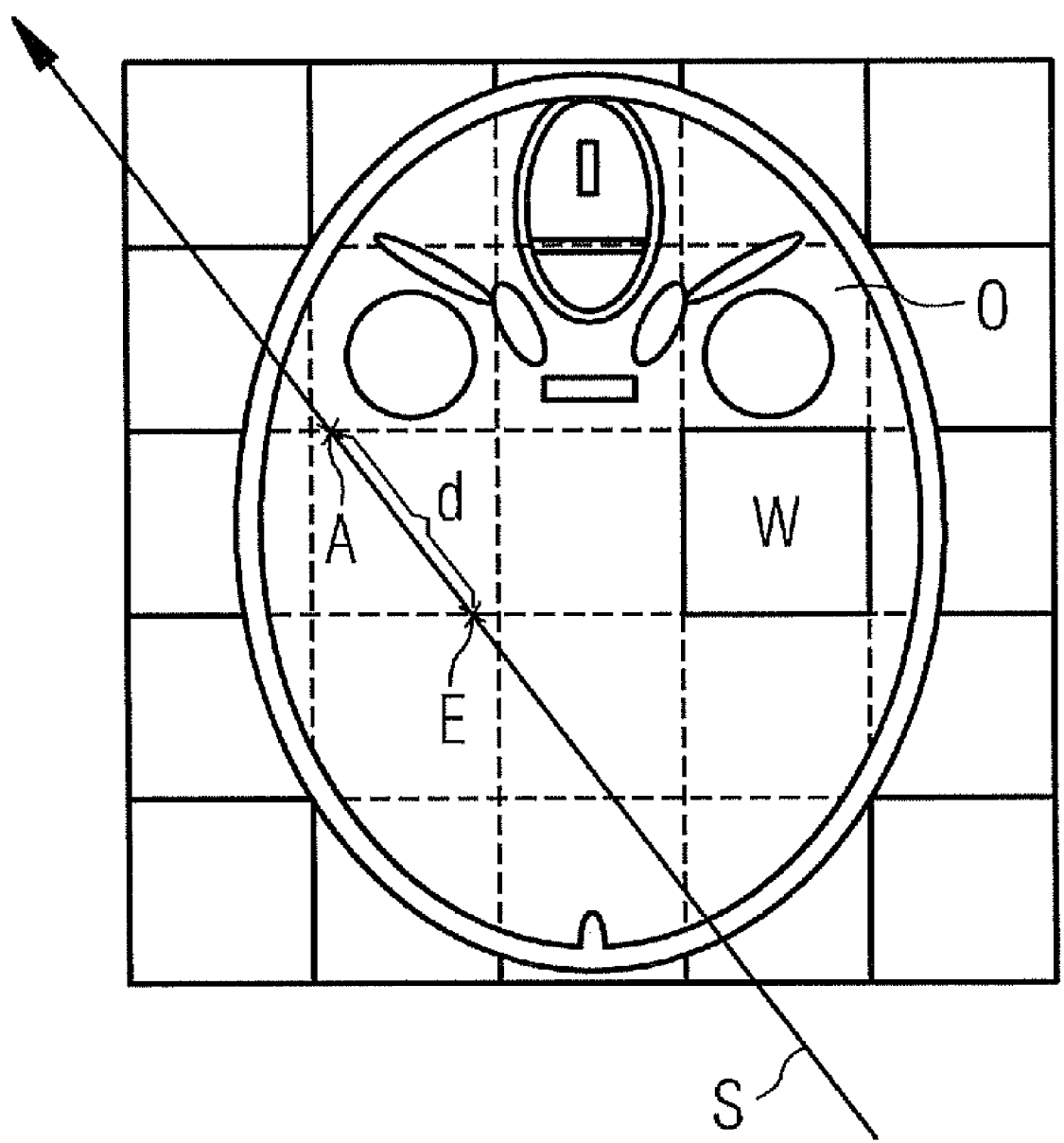
FIG. 5: Calculation of the line integral through a voxel

In FIG. 5 the relevant volume is divided into cubes. By way of example, one of the cubes W is highlighted. These cubes are selected here so that each of the cubes is assigned a voxel and thus an attenuation coefficient $\mu$. Using the attenuation coefficient, each cube can be assigned to a tissue class (segmentation). The thickness of an irradiated tissue class is then produced as the sum of the lengths d irradiated in the cubes passed, which in turn are obtained from entry point E and exit point A.

Figure 6:
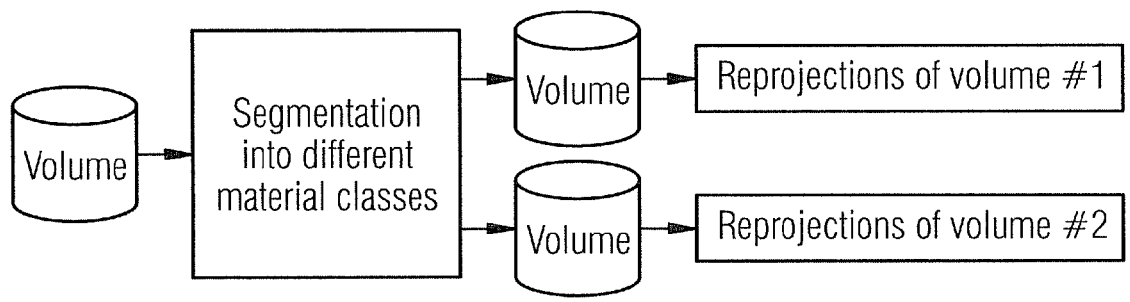
FIG. 6: Diagrammatic illustration of the previous approach
Figure 7:
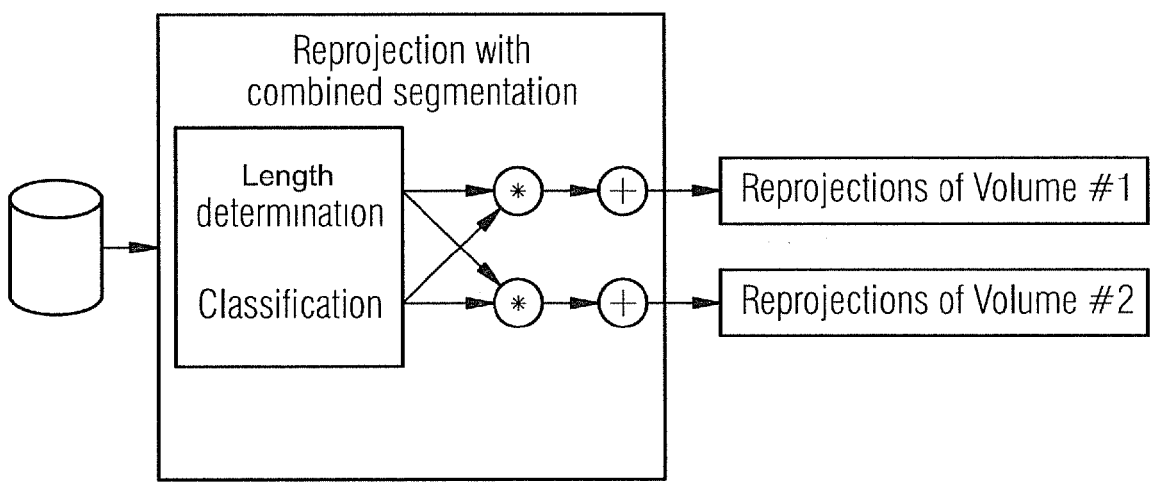
FIG. 7: Diagrammatic illustration of the new approach.

FIG. 6 and FIG. 7 contrast in diagrammatic form the conventional (FIG. 6) and the inventive (FIG. 7) method.

When using a simple segmentation method, such as for example a threshold-based segmentation method, the segmentation is consequently not performed until during the projection calculation, instead of segmenting the object before the projection calculation. If the projector is modified, the weight required for the relevant voxel and beam is determined. A decision is then taken by means of threshold value methods on the basis of the value of the pixel as to which projection value of a tissue class the weighted value of the pixel is added to. Additionally the irradiated material length can be updated correspondingly.

Moreover if it becomes necessary, as for example in the metal artifact correction method according to [Bal06], to calculate an additional model projection by a modified volume content, the requisite projection values can always still be carried out by means of a single projection step. However, for this it is necessary that the individual classes or values are encoded in the volume in a special form, which can then be decoded in the projection step. If for example as shown the model projection, in which the volume values in metal regions have been replaced by values of adjacent volume values, and the metal projections themselves are calculated, the values of the metal regions can be replaced by modified values of the model classes. This can be achieved for example by setting a bit or by adding an offset. As a result it is then possible to decide in the projection step itself the projection images for which the updates are to be performed. The corresponding values of the individual tissue classes (metal, metal tissue corrected to bone, etc.) can then be obtained from the given coding.

Should a more complex segmentation method be necessary, which cannot be performed during the projection calculation, the projection calculation of the individual tissue classes and/or models can nevertheless be performed in one step, in that—as described above—a decision as to which projection image of a tissue class the weighted value is added to is not made until during the projection calculation on the basis of the coding of the voxel value.

By using a pipeline structure the decision as to which of the two projections the weighted pixel value is added to, and the subsequent addition, can take place at the same time as the calculation of the next weight.

References:
Bu04 Buzug: Einfiihrung in the Computertomographie: 1. Auflage 2004 [Introduction to Computed Tomography: 1st edition]. Springer. ISBN 3-540-20808-9
Cas04 Van de Casteele: Model-based approached for Beam Hardening Correction and Resolution Measurements in Microtomography, Dissertation, University of Antwerp, 2004
Bal06 Bal and Spies: Metal artefact reduction in CT using tissue-class modeling and adaptive prefiltering, Med. Phys. 33(8), 2006
Sid85 Siddon: Fast calculation of the exact radiological path for a three-dimensional CT array, Medical Physics, 12(2): 252-255, March 1985
Mue98 Mueller: Fast and accurate three-dimensional reconstruction from Cone-Beam projection data using Algebraic Methods, Dissertation, Ohio State Univ., 1998

The invention claimed is:

1. A method for determining absorption coefficients for an object composed of a plurality of material types differing with absorption attributes, comprising:
recording a plurality of x-ray beam projections of the object with monochrome x-rays from different positions;
determining a first set of the absorption coefficients using a reconstruction method based on the recorded projections;
calculating a plurality of x-ray beam projections by a reprojection based on a formula-based description of a rule taking account of polychromy artifacts, wherein the rule involves a plurality of parameters to be determined, wherein the parameters vary based on different material types;
segmenting the first set of the absorption coefficients, wherein the segmenting comprises identifying at least a first material type in a path of each beam projection and determining for each beam projection a thickness consisting of said at least first material type;
in parallel with the calculating of the plurality of x-ray beam projections and the segmenting of the first set of the absorption coefficients, determining with the reprojection the plurality of parameters used by the rule to account for the polychromy artifacts and correcting the recorded projections based on the calculated projections; and
determining a second set of the absorption coefficients corrected with the polychromy artifacts using the reconstruction based on the corrected projections.

2. The method as claimed in claim 1, further comprising correcting metal artifacts by the reprojection during calculating the projections.

3. A device for determining absorption coefficients for an object composed of a plurality of material types differing with absorption attributes, comprising:
an x-ray device that records a plurality of x-ray beam projections of the object with monochrome x-rays from different positions; and
a computer that:
determines a first set of the absorption coefficients using a reconstruction method based on the recorded projections,
calculates a plurality of x-ray beam projections by a reprojection based on a formula-based description of a rule taking account of polychromy artifacts, wherein the rule involves a plurality of parameters to be determined, wherein the parameters vary based on different material types;
segments the first set of the absorption coefficients, wherein a segmentation of the first set of the absorption coefficients comprises identifying at least a first material type in a path of each beam projection and determining for each beam projection a thickness consisting of said at least first material type;
in parallel with a calculation of the plurality of x-ray beam projections and the segmentation of the volume of the object, determines with the reprojection the plurality of parameters used by the rule to account for the polychromy artifacts and corrects the recorded projections based on the calculated projections, and
determines a second set of the absorption coefficients corrected with the polychromy artifacts using the reconstruction based on the corrected projections.

4. A computer program stored on a non-transitory computer-readable media for determining absorption coefficients for an object composed of a plurality of material types differing with absorption attributes, comprising a computer code performing the following steps when executed by a computer:
determining a first set of the absorption coefficients using a reconstruction method based on a plurality of x-ray beam projections of the object recorded with monochrome x-rays from different positions;
calculating a plurality of x-ray beam projections by a reprojection based on a formula-based description of a rule taking account of polychromy artifacts, wherein the rule involves a plurality of parameters to be determined, wherein the parameters vary based on different material types;
segmenting the first set of the absorption coefficients, wherein a segmentation of the first set of the absorption coefficients comprises identifying at least a first material type in a path of each beam projection and determining for each beam projection a thickness consisting of said at least first material type;

in parallel with the calculating of the plurality of x-ray beam projections and the segmenting of the volume of the object, determining with the reprojection a plurality of parameters used by the rule to account for the polychromy artifacts and correcting the recorded projections based on the calculated projections; and determining a second set of the absorption coefficients corrected with the polychromy artifacts using the reconstruction based on the corrected projections.

* * * * *